United States Patent [19]
Faust et al.

[11] Patent Number: 6,121,442
[45] Date of Patent: Sep. 19, 2000

[54] 1,2-DIALKINYLATED COMPOUNDS

[75] Inventors: Rüdiger Faust; Christian Weber, both of Heidelberg, Germany

[73] Assignee: University of Heildelberg, Heidelberg, Germany

[21] Appl. No.: 09/029,877

[22] PCT Filed: Jun. 25, 1997

[86] PCT No.: PCT/EP97/03340

§ 371 Date: May 20, 1998

§ 102(e) Date: May 20, 1998

[87] PCT Pub. No.: WO98/00386

PCT Pub. Date: Jan. 8, 1998

[30] Foreign Application Priority Data

Jun. 28, 1996 [DE] Germany .......................... 196 26 120

[51] Int. Cl.$^7$ ................................................ C07D 487/22
[52] U.S. Cl. ............................................................ 540/145
[58] Field of Search ............................................. 540/145

[56] References Cited

U.S. PATENT DOCUMENTS 4,026,957  5/1977  Larock ................................. 260/666 A

FOREIGN PATENT DOCUMENTS 0685468    of 1995   European Pat. Off. .
0 685 468 A1  12/1995   European Pat. Off. .

OTHER PUBLICATIONS

Faust et al., Liebigs Annalew., 1996 pp. 1235–1238.
Preparation and Reactions of 2–Alkynyl–3–chloroquinoxalines;Donald E. Ames, John C. Mitchell, and Chisango C. Takundwa;J. Chem. Research (S). 1985, 144–145.
Cross–Coupling Reaction of Chloropyrazines with Acetylenes; Yasuo Akita, Akira Inoue, and Akihiro Ohta; Chem. Pharm. Bull. 34 (4) 1447–1458 (1986).
Alkynyl– and Dialkynyl–quinoxalines. Synthesis of Condensed Quinoxalines; Donald E. Ames and M. Ismail Brohi, J.C.S. Perkin I, 1384–1389.
Twards the total synthesis of cyclo[n]carbons and the generation of cyclo[6]carbon; George A. Adamson and Charles W. Rees, J. Chem. Soc.; 1535–1543; Perkin Trans. 1, 1996.
Novel and Convenient Routes to Functionalized Alkynyl Ketones from 1–(Benzotriazol–1–yl)propargyl Ethyls Ethers; Alan R. Katritzky and Hengyuan Lang; J. Org. Chem. 1995, 60, 7612–7618.
Preparation and Chemical Behavior of 2,3–Diethynyl–1, 3–butadiene;Henning Hopf, Marcus Theurig, Peter G. Jones, and Peter Bubenitschek; Liebigs Ann. 1996, 1301–1311.
Terminally Protected 1–Phenyl–1,5–hexadiyne–3,4–dionesas First Members of the Class of Dialkynyl–1,2–diones; Rüdiger Faust and Christian Weber; Liebigs Ann. 1996, 1235–1238.
Efficient Synthesis of Heteroradialenes by SN' Reaction; Rolf Gleiter, Harald Röckel, Hermann Irngartinger, and Thomas Oeser; Angew. Chem. Int. Ed. Engl. 1994, 33, No. 12.
Aliphatic Semidiones. XXX. Alkenyl and Cycloalkyl Substituted 1,2–Semidiones; Glen A. Russell, Marc Ballenegger, and Herbert L. Malkus; Journal of the American Society 97:7, 1900–1905, 1975.

*Primary Examiner*—Mukund J. Shah
*Assistant Examiner*—Pavanaram K Sripada
*Attorney, Agent, or Firm*—Hardaway/Mann IP Group Nexsen Pruet Jacobs & Pollard, LLP

[57] ABSTRACT

The present invention is relative to 1,2-dialkynylated compounds, especially dialkynyl-1,2-diones, a method of their production and their use as synthetic structural units to produce NIR dyes, pigments, thermostable polymers, charge-transfer complexes, heterocycles or pharmaceuticals.

3 Claims, 2 Drawing Sheets

IN HEXANE
$C = 1.5 \cdot 10^{-5}$ mol $l^{-1}$

FIG.1

IN CH$_2$Cl$_2$
C = 4.4 · 10$^{-6}$ mol l$^{-}$

Fig. 2

1,2-DIALKINYLATED COMPOUNDS

The present invention relates to 1,2-dialkynylated compounds, especially dialkynyl-1,2-diones, a method of their production and their use as synthetic structural units to produce NIR dyes, pigments, thermostable polymers, charge-transfer complexes, heterocycles or pharmaceuticals.

1,2-dialkynylated compounds represent synthons for chemical synthesis which can be transformed by very many different reactions in pharmaceutically effective compounds, dyes or pigments, thermostable polymers, electron acceptors in charge-transfer complexes or in other valuable chemical substances.

Up to the present, no vicinal diketones were known in the state of the art which are substituted on both carbonyl carbon atoms by alkynyl groups (called "dialkynyl-1,2-diones" in the following). This is surprising since such compounds are especially well-suited according to theoretical considerations for the production of α,β-dialkynyl-substituted heterocycles. Experiments to produce these desired compounds in a manner analogous to the synthesis of other 1,2-dione derivatives from oxalic acid derivatives (F. Babudri, V. Fiandanese, G. Marchese, A. Punzi: Tetrahedron Lett. (1995), 36, 7305–7308) such as e.g. from oxalylchloride or from 1,4-dimethylpiperazine-2, 3-dione (U. T. Mueller-Westerhoff, M. Zhou; J. Org. Chem. (1994) 59, 4988–4992) failed. In particular, no conversion of the metalated acetylides took place at low temperatures or overaddition to the tetra-alkinylated compounds, that is to the 1,2-diols, occurred under more vigorous conditions. Even the synthesis from trimethylsilyloxymethane phosphonates as masked equivalents of the corresponding acyl anions did not produce satisfactory results.

Thus, the present invention solves the problem of making available 1,2-dialkynylated synthons which can be used in the production of pharmaceutically effective compounds, dyes or pigments, thermostable polymers, electron acceptors in charge-transfer complexes or of other valuable chemical substances, as well as a method by which these synthons can be produced in a simple manner and in good yields.

This problem is solved by the embodiment characterized in the claims. In particular, compounds with the general formula (I) are made available (I)

in which the groups $R^1$ and $R^2$ can be identical or different and represent a hydrogen atom, a halogen atom, a straight-chain or branched-chain alkyl group with 1 to 6 carbon atoms, a cycloalkyl group with 3 to 7 carbon atoms which can comprise one or more heteroatoms, a substituted or unsubstituted aryl group which can comprise one or more heteroatoms, a mono-, di- or trialkylsilyl group with 1 to 6 carbon atoms independently of each other in each instance in the straight-chain or branched-chain alkyl group, a mono-, di- or triarylsilyl group with substituted or unsubstituted aryl groups independently of each other in each instance, an aralkyl group, an alkenyl group, an alkynyl group, an alkylthio group, an arylthio group, a trifluoromethyl-, ester-, carboxyl-, sulfonyl-, cyan-, alcohol-, aldehyde-, amino- or nitro group, or $R^1$ and $R^2$ form a ring together with 4 to 8 optionally substituted $CH_2$ groups, at least one $CH_2$ group of which can be replaced by an oxygen atom, a sulfur atom or an $NR^3$ group, with $R^3$ defined as defined below, X and Y can be identical or different and represent an oxygen atom, a sulfur atom, a dibromomethylene group, a dicyanomethylene group, an acyclic or cyclic O,O-ketenacetal group containing 2 to 3, optionally substituted, $CH_2$ groups, a substituted or unsubstituted 2-(1,3-dithiol-2-ylidene) group, a methylidene group substituted with a straight-chain or branched-chain alkyl group or with a cycloalkyl group or with a substituted or unsubstituted aryl group, a group with the following structures, a $PR^3$ group or an $NR^3$ group in which the group $R^3$ represents a hydrogen atom, a straight-chain or branched-chain alkyl group with 1 to 6 carbon atoms, a cycloalkyl group with 3 to 7 carbon atoms which can comprise one or more heteroatoms, a mono-, di- or trialkylsilyl group with 1 to 6 carbon atoms independently of each other in each instance in the straight-chain or branched-chain alkyl group, a mono-, di- or triarylsilyl group with aryl groups substituted independently from each other in each instance or unsubstituted, a straight-chain or branched-chain aliphatic, unsaturated, alicyclic, aromatic or aromatic heterocyclic group, or two $R^3$ groups represent a single bond or a ring together with at least one, e.g. 4 to 8, optionally substituted $CH_2$ group(s), or X represents an $NR^4$ group and Y an $NR^5$ group in which the groups $R^4$ and $R^5$ can be identical or different and represent a hydrogen atom, a mono-, di- or trialkylsilyl group with 1 to 6 carbon atoms independently of each other in the straight-chain or branched-chain alkyl group, a mono-, di- or triarylsilyl group with aryl groups substituted or unsubstituted independently of each other, a straight-chain or branched-chain aliphatic, alicyclic, aromatic or aromatic heterocyclic group, or X and Y form the following ring systems (A), (B), (C), (D) or (E):

(A)

-continued (B)

(C)

(D)

(E)

in which R¹ and R² are defined as above, in ring system (A) R⁶ and R⁷ can be identical or different and represent a hydrogen atom, a halogen atom, a straight-chain or branched-chain aliphatic, alicyclic, aromatic or aromatic heterocyclic group, an alkylthio group, an arylthio group, an isocyano-, isocyanato-, isothiocyanato-, trifluoromethyl-, ester-, carboxyl-, sulfonyl-, cyano-, alcohol-, aldehyde-, amino- or nitro group, in ring system (B) the anellated ring can comprise one, two or three nitrogen atom(s) and R⁸ represents a hydrogen atom, a halogen atom, a substituted or unsubstituted amino group, a hydroxy group, a carboxylate group, an ester group, an aldehyde group, a straight-chain or branched-chain aliphatic, alicyclic, aromatic or aromatic heterocyclic group, an alkylthio group, an arylthio group or a trifluoromethyl group, in ring system (C) R⁹ and R¹⁰ can be identical or different and represent a hydrogen atom, a halogen atom, a straight-chain or branched-chain aliphatic, alicyclic, aromatic or aromatic heterocyclic group, an alkylthio group, an arylthio group or a trifluoromethyl group, and Z represents an oxygen atom, a sulfur atom, a carbonyl group, a thiocarbonyl group, an alkylidene group, a methylene group, an NH group or an NR¹¹ group in which R¹¹ represents a straight-chain or branched-chain aliphatic, alicyclic, aromatic or aromatic heterocyclic group or an amino protective group, and in ring systems (D) and (E) the group R¹¹ has the previously cited definitions, wherein ring systems (B) and (C) can also be part of a larger aromatic or aromatic heterocyclic system.

Examples of compounds with a corresponding ring system (B) are cited below.

In a preferred embodiment of the present invention X and Y each represent an oxygen atom in compounds with general formula (I). In further preferred embodiments of the present invention X represents an NR³ group and Y an oxygen atom or X and Y each represent an NR³ group in compounds with general formula (I).

The groups R¹ or R² preferably represent a triisopropylsilyl group or an aryl group, especially a phenyl group, which aryl groups can be substituted singly or multiply, that is, once, twice or three times by an R' group or an OH, OR', Hal, NO₂, NH₂, NR'H, NR₂, CN, SO₃H, CO₂H, CO₂R' or CHO group. The R' group represents an alkyl group having 1 to 6 C atoms. The naphthyl-, anthracenyl- and fluorenyl groups can be considered with preference in addition to the phenyl group as further aryl groups.

R' and groups designated generally with "alkyl" can be an alkyl group selected from the group of methyl, ethyl, i- or n-propyl, i-, n- or t-butyl, 1-, 2- or 3-pentyl, 2-methylbutyl, 3-methylbutyl, 1,1-dimethylpropyl, 1,2-dimethylpropyl, 2,2-dimethylpropyl, n-, 2- or 3-hexyl, 2-, 3- or 4-methylpentyl, 2-methyl-2-pentyl, 2,2-dimethylbutyl, 3,3-dimethylbutyl, 2,3-dimethylbutyl, 3-methyl-2-pentyl, 2-methyl-2-pentyl, 2,3-dimethyl-2-butyl or 3,3-dimethyl-2-butyl, but especially an alkyl group selected from the group of methyl, ethyl, i- or n-propyl, i-, n- or t-butyl. Correspondingly, the alkylsilyl groups used in the compounds of the invention with general formula (I) are also preferably alkylsilyl groups substituted singly, twice or three times by methyl-, ethyl-, i- or n-propyl, i-, n- or t-butyl groups.

A substituent with the designation Hal shall represent a halogen atom from the group F, Cl, Br or I. Preferred halogen substituents are F, Cl, Br.

Further subject matter of the present invention is constituted by compounds with at least one structural unit (W), shown in the following, in which $R^1$ and $R^2$ have the previously cited definitions.

(W)

The structural unit (W) can be present e.g. in compounds of the tetraazafulvalene type (F) or in the corresponding para-quinoid systems (G) in which $R^1$, $R^2$ and $R^3$ have the previously cited definitions, provided that in formula (G) at least two vicinal $R^3$ groups can additionally form an optionally substituted, aromatic ring system with each other.

The structural unit (W) can be further complexed with a metal atom, e.g. under formation of a chelate complex. A metal atom in its appropriate oxidation stages, selected from Fe, Ni, Co, Cu, Pd, Pt, Ru, Ti and Zr is preferred thereby. Ni and Pd are especially preferred. Palladium complexes of formula (H), cited below, are especially preferred (H)

in which $R^3$ preferably represents a substituted or unsubstituted aryl group, which act e.g. as components of catalysts in olefin polymerization.

Figure 1:
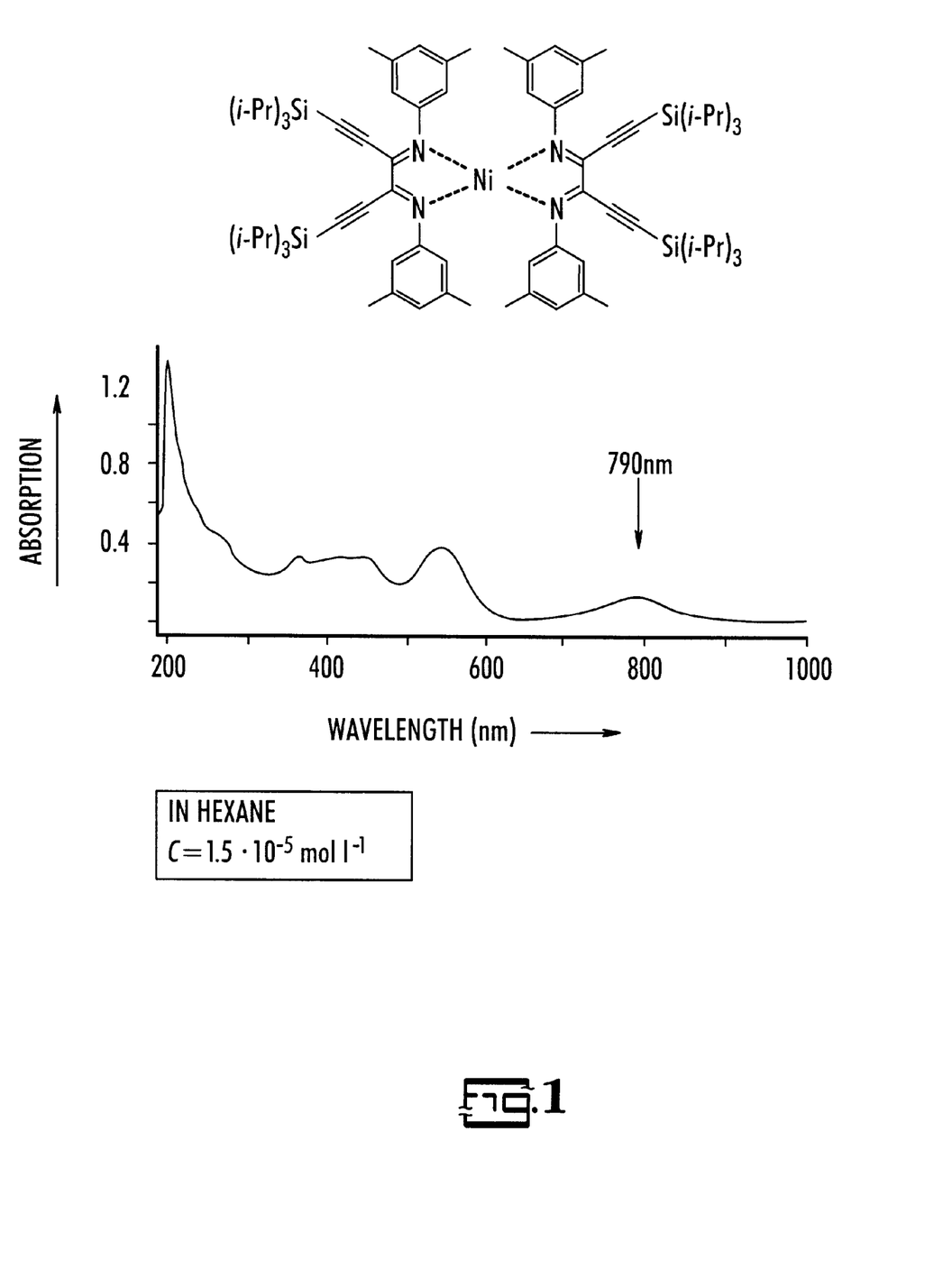

For example, structural unit (W) is also part of a nickel chelate according to compound (J) cited below, which has a longest wavelength absorption maximum at 790 nm.

(J)

FIG. 1 shows the UV/Vis absorption spectrum of compound (J) cited above.

Structural unit (W) is contained three times in corresponding Ru complexes.

Structural unit (W) can also be part of a macrocycle. E.g. phthalocyanin-, porphyrin structures or structures related to them can be considered as such a macrocycle. The macrocycle is preferably of the pyrazinoporphyrazine type of formula (K) shown below, in which $R^1$ and $R^2$ have the previously cited definitions.

(K)

Figure 2:
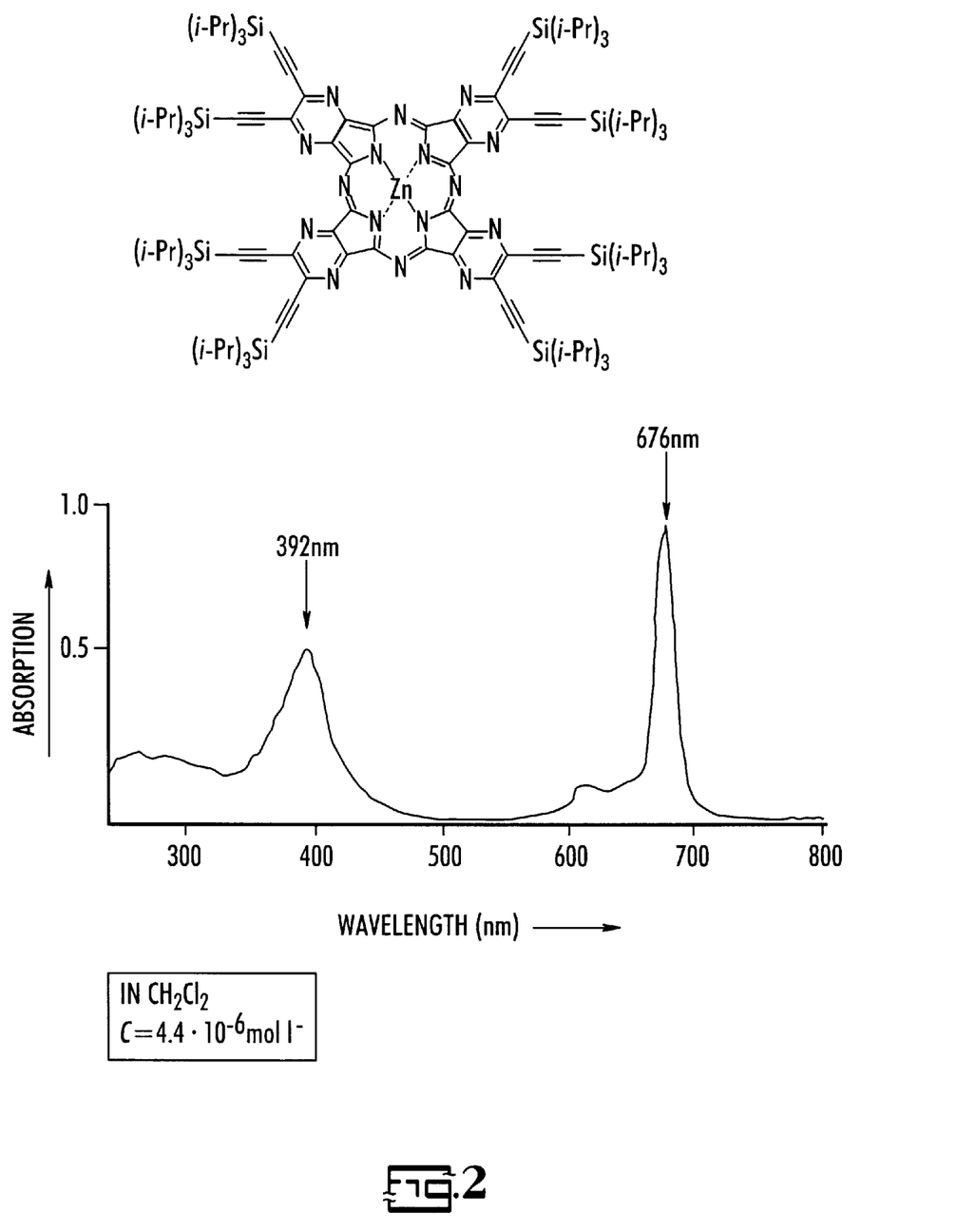

Compound (K) is more preferably complexed with a metal atom in its appropriate oxidation stages, e.g. Al, Ag, Co, Cu, Cr, Fe, Li, Mg, Mn, Ni, Pb, Pd, Rh, Ru, Si, Sn or Zn or with a metal compound such as TiO or VO. In compound (L), shown below, of the pyrazinoporphyrazine type the longest wavelength absorption maximum is approximately 676 nm.

(L)

FIG. 2 shows the UV/Vis absorption spectrum of compound (L).

One or two or three dialkynylpyrazine units can also be inserted into the macrocycle by the selection of the stoichiometry with different reaction partners of the dicyanopyrazine type, as is shown in the reaction cited below. This is an important advantage for the linking of several chromophore units via butadiyne bridges in order to produce strongly absorbent pigment dyes. The non-alkynylated dicyano component is not limited thereby to pyrazine derivatives.

The alkynylated macrocycles above are suitable to be used as laser dyes, as dyes in photodynamic cancer therapy or in liquid-crystal systems and also, on account of their non-linear optical properties, to be used as media for data storage based on optical principles and for the processing of data. Furthermore, they can be used as molecular organic semiconductors with applications as gas sensors, in photochromic systems, as color markers in environmental analysis or as a component of microelectronic systems.

Further subject matter of the present invention is constituted by making available a method of producing a compound of general formula (I) which comprises the following steps:

(a) The reaction of 1H-benzotriazole with a compound of the general formula (II)

(II)

in which group $R^1$ has one of the meanings defined above and R' is a substituted or unsubstituted alkyl group with 1 to 6 carbon atoms, to a compound with the formula (III) cited below (III)

in which Bt signifies 1H-benzotriazole-1-yl,

(b) The reaction of the compound (III) obtained in step (a) with a compound of the general formula (IV), (IV)

in which $R^2$ has one of the meanings defined above, to a compound of general formula (V)

(V)

in the presence of a lithium-organic compound,
(c) The oxidation of the compound (V) obtained in step (b) to a compound with the general formula (VI)

(VI)

and
d) The treatment of the compound (VI) obtained in step (c) with a dilute mineral acid.

The method in accordance with the invention is also suitable in its essential steps for the production of the corresponding higher homologues in accordance with the reaction scheme cited below.

Experiments have shown that a reactive compound with general formula (III) is obtained from a compound with the general formula (II) by replacing an alkoxy group with 1H-benzotriazole, which reactive compound with general formula (III) can be reacted in a simple reaction sequence to the compound of the invention with general formula (I).

In particular, the benzotriazole-substituted compound (III) can be produced according to a method like that described by Katritzky et al. in J. Org. Chem. (1995), 60 7612–7618.

Compound (III) can preferably be reacted in the presence of a lithium-organic compound such as n-butyllithium with carbaldehydes with general formula (IV) to an alkoxyalcohol of general formula (V), in which $R^1$, $R^2$, R' and Bt have the previously cited definitions. A mixture of the diastereomeric forms of this compound (III) in a ratio of approximately 1:1 is produced during this reaction, which is carried out in a solvent from the group tetrahydrofuran, dioxan, benzene, pentane, hexane and diethyl ether or mixtures thereof at temperatures of –85 to 0° C., especially at –80 to –70 ° C.

The desired compound with general formula (I) can be produced in a simple manner from compound (V) obtained; however, it must be taken into consideration that compound (V) is very sensitive to acid on account of the propargyl alcohol group. Accordingly, all attempts to produce a corresponding dialkynyl-α-hydroxyketone from the compound with general formula (V) by cleaving the alkoxy group and by simultaneously removing the benzotriazole group in the presence of dilute acids have not been successful. Even the action of oxidizing agents based on chromium compounds such as e.g. pyridinium chlorochromates or pyridinium bichromates resulted only in the decomposition of initial compound (V).

It was determined in accordance with the invention that it is surprisingly possible to oxidize the alcoholic group in compound (V) under mild conditions in the presence of Dess-Martin periodinane, producible according to a method like that described in J. Am. Chem. Soc. (1991) 113, 7277–7287, or like that of Ireland and Lio in J. Org. Chem. (1993) 58, 2899, to the corresponding keto group. In order to carry out this oxidation the previously produced alkoxyalcohol (V) is dissolved in an aprotic solvent, especially in dichloromethane. The oxidation of the alcoholic group to a keto group takes place at a temperature of 0 to 60° C., preferably 15 to 35 ° C.

The monoketone (VI) obtained in this manner is so stable that a conversion of the alkoxy group into the corresponding keto group in the presence of a dilute acid from the group of hydrochloric acid, sulfuric acid, nitric acid and phosphoric acid, p-toluene sulfonic acid, especially hydrochloric acid, in an aprotic solvent from the group of acetone, tetrahydrofuran, dioxan, diethyl ether, carbon tetrachloride, hexane, benzene, nitrobenzene, dimethyl formamide and dimethyl sulfoxide is possible under careful monitoring of the reaction temperature. Monitoring of the reaction temperature means in this connection that the temperature must be maintained in a range of –10 to 25° C. as a function of the desired reaction. The reaction takes place especially well in a temperature range of 0 to 10 ° C. It is recommended, especially in the case of sensitive substrates, to keep the temperature at approximately 5 ° C.

The acids which can be used for the hydrolysis are advantageously not diluted with water but rather with the same solvent in which monoketone compound (VI) to be hydrolyzed had also been dissolved. This preferably concerns aprotic solvents like acetone, tetrahydrofuran, dioxan, diethyl ether, carbon tetrachloride, hexane, benzene, nitrobenzene, dimethyl formamide or dimethyl sulfoxide.

The compounds with general formula (I), especially those comprising the substituents on the aryl group, which can cause problems during the actual production method can also be compounds whose substituents are provided with protective groups which can be removed again by solvolysis or hydrolysis after the reaction has taken place. This can also not take place until after the further reaction to desired resultant products from compounds of formula (I).

If possible, the synthesis of a compound (I) is carried out in such a manner that a solvolysis to release the desired compound (I) is eliminated, especially since a compound of this structure frequently exhibits an unstable behavior under such conditions.

Preferred initial materials for the solvolysis or hydrogenolysis are those which correspond to the formulas cited above but contain, instead of free amino- and/or hydroxy groups, corresponding protected amino- and/or hydroxy groups, preferably those which carry an amino protective group instead of an H atom connected to an N atom, especially those which carry an R'''—N group instead of an HN group, in which R'''—N group R'' represents an amino protective group, and/or those which carry a hydroxy protective group at the position of the H atom, e.g. those which carry a —COOR''' group instead of a —COOH group, in which —COOR''' group R''' represents a hydroxy protective group.

Even several protected amino and/or hydroxy groups which are identical or different from each other can be present in the molecule of the initial material. If the protective groups present are different from each other they can be selectively split off.

The expression "amino protective groups" is generally known and refers to groups which are suitable for protecting (blocking) an amino group from chemical reactions but which can be readily removed after the desired chemical reaction has been carried out at another location of the molecule. In particular, unsubstituted or substituted acyl-, aryl- (e.g. dinitrophenyl (DNP)), aralkoxymethyl- (e.g. benzoxymethyl (BOM)) or aralkyl groups (e.g. benzyl, 4-nitrobenzyl, triphenylmethyl) are typical for such groups. Since the amino protective groups are removed after the desired reaction (or reaction sequence), their kind and size is, for the rest, not critical. However, those with 1 to 20, especially 1 to 8 C atoms are preferred. The expression "acyl group" is to be construed in the broadest sense in conjunction with the present method. It comprises acyl groups derived from aliphatic, araliphatic, aromatic or heterocyclic carboxylic acids or sulfonic acids as well as comprises in particular alkoxycarbonyl-, aryloxycarbonyl- and above all aralkoxycarbonyl groups. For example, alkanoyl groups such as the acetyl-, propionyl-, butyryl group, aralkanoyl groups such as the phenacetyl group, aroyl groups such as the benzoyl- or toloyl group, aryloxyalkanoyl groups such as the phenoxyacetyl group, alkoxycarbonyl groups such the methyoxycarbonyl-, ethoxycarbonyl group, the 2,2,2-trichloroethoxycarbonyl-, the isopropoxycarbonyl-, the tert.-butoxycarbonyl-(BOC), the 2-iodoethoxycarbonyl group and aralkyloxycarbonyl groups such as the benzoyloxycarbonyl- (CBZ), the 4-methoxybenzyloxycarbonyl- and the 9-fluorenylmethoxycarbonyl group (FMOC) can be considered for such acyl groups. Preferred amino protective groups are the BOC-, DNP- and BOM-, furthermore, the CBZ, benzyl- and acetyl group.

The expression "hydroxy protective group" is also generally known and refers to groups which are suitable for protecting a hydroxy group from chemical reactions but which can be readily removed after the desired chemical reaction has been carried out at another location of the molecule. Unsubstituted or substituted aryl-, aralkyl- or acyl groups, furthermore, also alkyl groups are typical for such groups. The nature and size of the hydroxy protective groups is not critical since they are removed again after the desired chemical reaction or reaction sequence. Groups with 1 to 20, especially 1 to 10 C atoms are preferred. Examples for hydroxy protective groups are, among others, the tert.-butyl-, benzyl-, p-nitrobenzoyl-, p-toluene sulfonyl- and acetyl protective group with the benzyl protective group and the acetyl protective group being especially preferred.

The functional derivatives of the compounds with general formula (I) which are to be used as initial substances can be produced according to the customary methods as they are described e.g. in the appropriate standard works and in the pertinent patent literature, e.g. by reacting compounds corresponding to formulas (II) and (IV); however, at least one of these compounds carries a protective group instead of an H atom.

The "releasing" of the compounds with general formula (I) in accordance with the invention from their functional derivatives succeeds, depending on the protective group used, e.g. by hydrogenolysis or with strong acids, purposefully with trifluoroacetic acid or perchloric acid but also with other strong, inorganic acids such as hydrochloric acid or sulfuric acid, with strong organic carboxylic acids such as trichloroacetic acid or sulfonic acids such as benzene sulfonic acid or p-toluene sulfonic acid. The presence of an additional solvent is possible but not always necessary.

For example, carboxylic acids such as acetic acid, ethers such as tetrahydrofuran (THF) or dioxan, amides such as dimethyl formamide (DMF), furthermore, also alcohols such as methanol, ethanol or isopropanol as well as water are suitable as solvent. Furthermore, mixtures of the previously cited solvents can be considered. Trifluoroacetic acid is preferably used in an excess without the addition of a further solvent and perchloric acid, on the other hand, in the form of a mixture of acetic acid and 70% perchloric acid in a ratio of 9:1. The reaction temperature for the splitting off of protective groups is advantageously between approximately 0 and 50° C. The reaction temperature is preferably between 15 and 30° C. ("room temperature").

The BOC group can be split off e.g. preferably with 40% trifluoroacetic acid in dichloromethane or with approximately 3 to 5 N HCl in dioxan at 15 to 60° C. and the FMOC with an approximately 5 to 20% solution of dimethyl amine, diethyl amine or piperidine in DMF at 15 to 50 ° C. A splitting off of the DNP group also succeeds e.g. with an approximately 3 to 10% solution of 2-mercaptoethanol in DMF/water at 15 to 30° C.

Hydrogenolytically removable protective groups (e.g. the BOM-, CBZ- or benzyl group) can be split off e.g. by treatment with hydrogen in the presence of a catalyst (e.g. a noble-metal catalyst such as palladium, advantageously on a carrier such as carbon). Suitable solvents thereby are the previously indicated solvents, especially e.g. alcohols such as methanol or ethanol or amides such as DMF. The hydrogenolysis is carried out usually at a temperature between 0 and approximately 100° C. and a pressure between approximately 1 and 200 bar, preferably at 20 to 30° C. and 1 to 10 bar. A hydrogenolysis of the CBZ group succeeds e.g. well on 5 to 10% Pd-C in methanol at 20 to 30° C.

Depending on which $R^1$ and $R^2$ groups are located in the position adjacent to the triple bond, the compounds with general formula (I) produced in accordance with the method of the invention are more or less stable compounds which are especially well-suited for the production of cyclic compounds which are substituted on vicinal carbon atoms by alkynyl groups. It is therefore advantageous on account of the physical properties to react these novel compounds with general formula (I) after the isolation directly in a subsequent reaction.

The method of the invention can furthermore comprise a condensation with primary mono- or diamines after step (d). For example, the condensation can be carried out with 1,2-diaminomaleic dinitrile, o-phenylene diamine, 2,3-diaminopyridine, 3,4-diaminopyridine or 5,6-diaminopyrimidine. The condensation is normally carried out in a solvent selected from tetrahydrofuran, dioxan, benzene, toluene, xylene, hexane, diethyl ether and acetic acid, optionally under the action of a Lewis acid such as e.g. titanium tetrachloride, preferably in a temperature range of −80 to 150° C.

Stable representatives of the compounds according to formula (I) with X,Y=O (dialkynyl-1,2-diones) are the compounds with $R^1$, $R^2$=Si(i-Pr)$_3$, $R^1$=Ph, $R^2$=Si(i-Pr)$_3$, $R^1$, $R^2$=Ph, $R^1$=Ph, $R^2$=t-Bu, $R^1$=Ph, $R^2$=SiMe$_3$. They can be stored cooled in pure form for several weeks. In contrast thereto, other dialkynyl-1,2-diones slowly decompose in the presence of air. Corresponding dialkynyl-1,2-diones in which e.g. $R^1$ and $R^2$ represent trialkylsilyl groups, especially trimethylsilyl groups, are sensitive and readily react to external conditions such as e.g. to atmospheric oxygen and to moisture to which they are exposed.

Corresponding acyclic and cyclic compounds derived from the compounds of the invention with formula (I) can have valuable pharmaceutical properties and also be used as intermediate products for producing α,β-dialkynyl-substituted acyclic, cyclic or heterocyclic compounds, which cyclic compounds can also have an aromatic character, pharmaceuticals, thermostable polymers, dyes, especially NIR dyes, pigments or compounds which function as electron acceptors in charge-transfer complexes.

Compounds with formula (I) in which $R^1$ and $R^2$ each represent a hydrogen atom, especially those compounds derived from the aromatic nitrogen heterocycles of the previously cited ring systems (A) to (E), are significant as pharmaceuticals such as antitumor agents or antibiotics on account of the endiyne unit integrated into the cycle, which unit can damage or split DNA as a consequence of the mechanism of action of the Bergman cyclization, and of the aromatic, nitrogen-substituted heterocycle characterized by especially good DNA intercalation properties (see K. C. Nicolaou in Modem Acetylene Chemistry, P. J. Stang, F. Diederich editors), VCH, Weinheim, 1996).

The present invention is explained further in the following examples of the invention.

EXAMPLE 1

General Preparation of Compounds with General Formula (V)

1.8 mmol n-butyllithium dissolved in hexane (1.2 ml of a 1.6 M solution) are added to a solution cooled to a temperature of −78° C. and consisting of 500 mg (1.8 mmol) 1-(1-ethoxy-3-phenyl-prop-2-ynyl)-1 H benzotriazole and 80 ml tetrahydrofuran. The color of the solution turns dark blue. After 5 minutes of agitation 3 mmol of the corresponding propargylaldehyde (IV) are added. The solution is maintained at a temperature of −78° C. for 5 minutes and is subsequently quenched/hydrolyzed at this temperature with 40 ml water. The mixture obtained in this manner is extracted three times with 50 ml diethyl ether. The combined etheral phases are dried over sodium sulfate. After the filtering and distilling the solvent a yellowish brown oil is obtained which is purified chromatographically on a column packed with silica gel with a solvent mixture consisting of hexane and ethyl acetate in a ratio of 2:1. A pale yellow oil is obtained in this manner which is composed of a diastereomeric mixture of the desired products. The pure compounds can be crystallized as colorless solids out of a solvent mixture consisting of diethyl ether and hexane in a ratio of 5:1. The following products were produced in this manner:

a) 4-(benzotriazol-1-yl)-4-ethoxy-1,6-diphenyl-hexa-1,5-diyn-3-ol ($R^1$=phenyl, $R^2$=phenyl) Yield: 360 mg (50% of theory), colorless solid, Melting point: 160–161° C. IR(KBr); v=3416 cm$^{-1}$ (m) (OH), 2925 (m)(CH), 2235 (m)(C≡C)

b) 6-(benzotriazol-1-yl)-6-ethoxy-2,2-dimethyl-8-phenyl-octa-3,7-diyn-5 -ol ($R^1$=phenyl, $R^2$=t-butyl) Yield: 385 mg (55% of theory), colorless solid, Melting point: 154–155° C. IR(KBr): v=3446 cm$^{-1}$ (m)(OH), 2968 (m)(CH), 2882 (w)(CH), 2236 (m)(C≡C)

c) 4-benzotriazol-1-yl)-4-ethoxy-6-phenyl-1-trimethylsilyl-hexa-1,5-diyn-3-ol ($R^1$=phenyl, $R^2$=trimethylsilyl) Yield: 120 mg (17% of theory), colorless solid, Melting point: 167–168° C. IR(KBr): v=3438 cm$^{-1}$ (m)(OH), 2969 (m)(CH), 2881 (w)(CH), 2237 (m)(C≡C)

d) 4-(benzotriazol-1-yl)-4-ethoxy-6-phenyl-1-triisopropylsilyl-hexa-1,5-diyn-3-ol ($R^1$=phenyl, $R^2$=triisopropylsilyl) Yield: 350 mg (40% of theory), colorless solid, Melting point: 128–129° C. IR(KBr): v=3365 cm$^{-1}$ (m)(OH), 2942 (m)(CH), 2864 (w)(CH), 2239 (m)(C≡C)

EXAMPLE 2

General Preparation of Compounds with General Formula (VI)

410 mg (1.1 mmol) Dess-Martin periodinane are added under agitation to a solution consisting of 50 ml dichloromethane and 1 mmol of a 1,5-hexadiyn-3-ol produced according to example 1. After one hour agitation at room temperature the reaction mixture obtained is hydrolyzed with 40 ml water. It is extracted three times with 50 ml diethyl ether. The combined ether phases are dried over sodium sulfate. After filtering and distilling the solvent a raw product is obtained from which the pure substances are obtained as viscous oils by flash chromatography on a silica gel column with ethyl acetate as eluent. The pure substances can be optionally obtained in crystalline form from a solvent mixture consisting of diethyl ether/hexane in a ratio of 5:1.

The following products were produced in this manner:

a) 4-(benzotriazol-1-yl)-4-ethoxy-1,6-diphenyl-hexa-1,5-diyn-3-one ($R^1$=phenyl, $R^2$=phenyl) Yield: 320 mg (80% of theory), pale yellow solid, Melting point: 111–112° C. IR(KBr): v=2981 cm$^{-1}$ (m)(CH), 2198 (s)(C≡C), 1700 (s)(CO)

b) 6-(benzotriazol-1-yl)-6-ethoxy-2,2-dimethyl-8-phenyl-octa-3,7-diyn-5 -one ($R^1$=phenyl, $R^2$=t-butyl) Yield: 300 mg (78% of theory), pale yellow oil IR(film):

v=2976 cm$^{-1}$ (m)(CH), 2897 (m)(CH), 2230 (m) (C≡C), 1701 (s)(CO)

c) 4-(benzotriazol-1-yl)-4-ethoxy-6-phenyl-1-trimethylsilyl-hexa-1,5-diyn-3 -one (R$^1$=phenyl, R$^2$=trimethylsilyl) Yield: 80 mg (15% of theory), yellow oil, IR(film): v=2927 cm$^{-1}$ (m)(CH), 2840 (m) (CH), 2229 (m)(C≡C), 2152 (w)(C≡C), 1701 (s)(CO)

d) 4-benzotriazol-1-yl)-4-ethoxy-6-phenyl-1-triisopropylsilyl-hexa-1,5-diyn- 3-one (R$^1$=phenyl, R$^2$=triisopropylsilyl) Yield: 390 mg (80% of theory), pale yellow oil IR(film): v=2944 cm$^{-1}$ (s)(CH), 2866 (s)(CH), 2230 (m)(C≡C), 2150 (m)(C≡C), 1705 (s) (CO)

EXAMPLE 3

General Preparation of Compounds with General Formula (I)

1 mmol of a hexa-1,5-diyn-3-one produced according to example 2 is dissolved in 20 ml acetone. To this solution, which had previously been cooled to a temperature of 5° C. is added under agitation a likewise cooled solution consisting of 5 ml acetone and 0.5 ml 37% hydrochloric acid. The reaction mixture obtained in this manner is agitated for 30 minutes, during which it becomes warmer. 100 ml diethyl ether and 40 ml water are added sequentially under agitation. After the organic and the aqueous phases have separated from one another the aqueous phases are extracted three times with 50 ml diethyl ether. The organic phases are combined, washed twice with 50 ml concentrated sodium carbonate solution and dried over sodium sulfate. The solution obtained in this manner is then filtered and the solvent distilled. The raw product obtained in this manner is a yellow, viscous oil. The pure products can be isolated by column chromatography on silica gel with a solvent mixture consisting of hexane and ethyl acetate in a ratio of 10:1. If necessary, the products accumulating as oil can be obtained in crystalline form from a solvent consisting of diethyl ether and hexane in a ratio of 5:1.

The following products were produced in this manner:

a) 1,6-diphenyl-hexa-1,5-diyne-3,4-dione (R$^1$ =phenyl, R$^2$ =phenyl) Yield: 190 mg (75% of theory), deep yellow solid, Melting point: 110–111° C. IR(film): v=2925 cm$^{-1}$ (w)(CH), 2190 (s)(C≡C), 1653 (s)(CO)

b) 8-phenyl-2,2-dimethyl-octa-3,7-diyne-5,6-dione (R$^1$= phenyl, R$^2$=t-butyl) Yield: 170 mg (70% of theory), yellow oil, IR(film): v=2973 cm$^{-1}$ (m)(CH), 2870 (w)(CH), 2201 (s)(C≡C), 1673 (s)(CO)

c) 1-phenyl-6-trimethylsilyl-hexa-1,5-diyne-3,4-dione (R$^1$=phenyl, R$^2$=trimethylsilyl) Yield: 38 mg (15% of theory), yellow oil, IR(film): v=2961 cm$^{-1}$ (m)(CH), 2195 (s)(C≡C), 2152 (w)(C≡C), 1673 (s)(CO)

d) 1-phenyl-6-triisopropylsilyl-hexa-1,5-diyne-3,4-dione (R$^1$ =phenyl, R$^2$=triisopropylsilyl) Yield: 220 mg (65% of theory), yellow oil, IR(film): v=2945 cm$^{-1}$ (m)(CH), 2867 (m)(CH), 2195 (s)(C≡C), 2147 (w)(C≡C), 1675 (s)(CO)

e) 1,6-bis(triisopropylsilyl)-hexa-1,5-diyne-3,4-dione (R$^1$=triisopropylsilyl, R$^2$ =triisopropylsilyl) Yield: 90% of theory, yellow oil IR(film): v=2946 cm$^{-1}$ (s)(CH), 2868 (s), 2146 (m) (C≡C), 1678 (s)(CO)

EXAMPLE 4

Preparation of 2,3-dicyano-5-(triisopropylsilylethynyl)-6-phenylethynyl pyrazine

100 mg (0.24 mmol) 1-phenyl-6-triisopropylsilyl-hexa-1, 5-diyne-3,4-dione are taken up in 50 ml acetonitrile and compounded with 26 mg (0.24 mmol) 1,2-diaminomaleic-acid nitrile. The solution is heated to reflux temperature and agitated 12 hours. The solvent is subsequently distilled in the vacuum of a rotary evaporator. The residue obtained is purified chromatographically with a solvent mixture consisting of hexane and ethyl acetate in a ratio of 5:1 as elution agent on a column filled with silica gel. The product is obtained by recrystallization out of a solvent mixture consisting of hexane and methylene chloride in a ratio of 5:1.

Yield: 40 mg 2,3-dicyano-5-(triisopropylsilylethynyl)-6-phenylethynyl pyrazine (40% of theory), orange-colored crystals Melting point: 151–152° C. IR(KBr): v=2949 cm$^{-1}$ (m)(CH), 2864 (m)(CH), 2208 (s)(C≡C, C≡N)

2,3-dicyano-5,6-bis(-phenylethynyl) pyrazine (orange-colored crystals) was produced in an analogous manner. Melting point: 226–227° C.

That which is claimed is:

1. The compound with the general formula comprising:

(K)

wherein R$^1$ and R$^2$ can be identical or different and represent a hydrogen atom, a halogen atom; a straight-chain or branched-chain alkyl group with 1 to 6 carbon atoms; a cycloalkyl group with 3 to 7 carbon atoms which can comprise one or more heteroatoms; a substituted or unsubstituted aryl group which can comprise one or more heteroatoms; a mono-, di-, or trialkylsilyl group with 1 to 6 carbon atoms independently of each other in each instance in the straight-chain or branched-chain alkyl group; a mono-, di-, or triarylsilyl group with substituted or unsubstituted aryl gropus independently of each other in each instance; an aralkyl group; an alkenyl group; an alkynyl group; an alkylthio group; an arylthio group; a trifluoromethyl-, ester-, carboxyl-, sulfonyl-, cyan-, alcohol-, aldehyde-, amino-, or nitro-group; or R$^1$ and R$^2$ form a ring together with 4 to 8 substituted or unsubstituted CH$_2$ groups, at least one CH$_2$ group of which can be replaced by an oxygen atom, a sulfur atom, or an NR$^3$ group; and wherein R$^3$ represents a hydrogen atom; a straight-chain or branched chain alkyl group with 1 to 6 carbon atoms; a cycloalkyl group with 3 to 7 carbon atoms which can comprise one or more heteroatoms; a mono-, di-, or trialkylsilyl group with 1 to 6 carbon atoms independently of each other in each instance in the straight-chain or branched-chain alkyl group; a mono-, di-, or triarylsilyl group with aryl groups substituted independently of each other in each instance or unsubstituted; a straight-chain or branched-chain aliphatic, unsaturated, alicyclic, aromatic or aromatic heterocyclic group; or two $R^3$ groups represent a single bond or ring together with at least one substituted or unsubstituted $CH_2$ group.

2. The compound according to claim 1, wherein the compound with general formula (K) is complexed with a metal atom in its appropriate oxidation stage, said metal atom selected from the group consisting of Al, Ag, Co, Cu, Cr, Fe, Li, Mg, Mn, Ni, Pb, Pd, Rh, Ru, Si, Sn, and Zn, or with a metal compound selected from TiO or VO.

3. The compound according to claim 2 comprising the following formula (L)

wherein M is Mg or Zn.

* * * * *